US011179177B2

(12) United States Patent
Olson

(10) Patent No.: US 11,179,177 B2
(45) Date of Patent: Nov. 23, 2021

(54) ULTRASONIC BLADE AND CLAMP ARM MATCHING DESIGN

(71) Applicant: Ethicon LLC, Guaynabo, PR (US)

(72) Inventor: William A. Olson, Lebanon, OH (US)

(73) Assignee: Cilag GmbH International, Zug (CH)

( * ) Notice: Subject to any disclaimer, the term of this patent is extended or adjusted under 35 U.S.C. 154(b) by 128 days.

(21) Appl. No.: 16/398,621

(22) Filed: Apr. 30, 2019

(65) Prior Publication Data

US 2020/0345390 A1 Nov. 5, 2020

(51) Int. Cl.
*A61B 17/32* (2006.01)
*A61B 18/12* (2006.01)
(Continued)

(52) U.S. Cl.
CPC .. *A61B 17/320092* (2013.01); *A61B 18/1206* (2013.01); *A61B 18/1445* (2013.01);
(Continued)

(58) Field of Classification Search
CPC ....... A61B 2017/320078; A61B 2017/320094; A61B 2017/320095; A61B 17/320092; A61B 17/320068; A61B 2017/2829; A61B 2017/2825; A61B 17/282; A61B 18/1206; A61B 18/1445; A61B 2018/00589; A61B 2018/00601; A61B 2018/00607; A61B 2018/0063; A61B 2018/00875; A61B 2017/320074; A61B 2017/320093; A61B 17/29; A61B 17/2812; A61B 17/2804
See application file for complete search history.

(56) References Cited

U.S. PATENT DOCUMENTS 5,322,055 A 6/1994 Davison et al.
5,324,299 A 6/1994 Davison et al.
(Continued)

FOREIGN PATENT DOCUMENTS

DE 103 20 412 A1 11/2004
EP 1946708 B1 6/2011

OTHER PUBLICATIONS

U.S. Appl. No. 61/410,603, entitled "Energy-Based Surgical Instruments," filed Nov. 5, 2010.
(Continued)

*Primary Examiner* — Tan-Uyen T Ho
*Assistant Examiner* — Bridget E. Rabaglia
(74) *Attorney, Agent, or Firm* — Frost Brown Todd LLC

(57) ABSTRACT

An ultrasonic surgical instrument includes a shaft assembly and an end effector. The end effector extends extending distally from the shaft assembly and includes an ultrasonic blade, a clamp arm, and a clamp pad. The clamp arm is movably secured relative to the ultrasonic blade and includes a mortise longitudinally extending therethrough. The clamp pad is connected to the clamp arm. The clamp arm includes a pad body and a tenon. The pad body extends in a longitudinal direction and is configured to compress a tissue toward the ultrasonic blade. The tenon is secured to the pad body and is received within the mortise. The tenon includes a rail, a support base, and a plurality of openings. The plurality of openings extends through at least one of the support base or the rail such that the tenon has a predetermined transverse spring rate longitudinally along the tenon.

20 Claims, 9 Drawing Sheets

(51) Int. Cl.
*A61B 18/14* (2006.01)
*A61B 18/00* (2006.01)

(52) U.S. Cl.
CPC ............. *A61B 2017/320074* (2017.08); *A61B 2017/320093* (2017.08); *A61B 2017/320094* (2017.08); *A61B 2017/320095* (2017.08); *A61B 2018/0063* (2013.01); *A61B 2018/00589* (2013.01); *A61B 2018/00601* (2013.01); *A61B 2018/00607* (2013.01); *A61B 2018/00875* (2013.01)

(56) References Cited

U.S. PATENT DOCUMENTS

| | | | |
|---|---|---|---|
| 5,776,155 | A | 7/1998 | Beaupre et al. |
| 5,873,873 | A | 2/1999 | Smith et al. |
| 5,938,633 | A | 8/1999 | Beaupre |
| 5,980,510 | A | 10/1999 | Tsonton et al. |
| 6,214,023 | B1 | 4/2001 | Whipple et al. |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |
| 6,500,176 | B1 | 12/2002 | Truckai et al. |
| 6,773,444 | B2 | 8/2004 | Messerly |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,189,233 | B2 | 3/2007 | Truckai et al. |
| 7,186,253 | B2 | 5/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 7,544,200 | B2 | 6/2009 | Houser |
| 8,057,498 | B2 | 11/2011 | Robertson |
| 8,461,744 | B2 | 6/2013 | Wiener et al. |
| 8,591,459 | B2 | 11/2013 | Clymer et al. |
| 8,591,536 | B2 | 11/2013 | Robertson |
| 8,623,027 | B2 | 1/2014 | Price et al. |
| 8,663,220 | B2 | 3/2014 | Wiener et al. |
| 8,911,460 | B2 | 12/2014 | Neurohr et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,381,058 | B2 | 5/2016 | Houser et al. |
| 9,393,037 | B2 | 7/2016 | Olson et al. |
| 9,795,379 | B2 | 10/2017 | Leimbach et al. |
| 9,949,785 | B2 | 4/2018 | Price et al. |
| 10,034,685 | B2 | 7/2018 | Boudreaux et al. |
| 10,172,636 | B2 | 1/2019 | Stulen et al. |
| 10,206,705 | B2 | 2/2019 | Estera et al. |
| 10,327,797 | B2 | 6/2019 | Conlon et al. |
| 10,492,820 | B2 | 12/2019 | Hibner et al. |
| 10,507,033 | B2 | 12/2019 | Dickerson et al. |
| 10,792,064 | B2 | 10/2020 | Craig et al. |
| 2002/0111650 | A1* | 8/2002 | Fogarty ................ A61B 17/282 606/207 |
| 2003/0181932 | A1* | 9/2003 | Buelna ................ A61B 17/122 606/158 |
| 2004/0167552 | A1* | 8/2004 | Buelna ................ A61B 17/122 606/158 |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0105750 | A1 | 4/2009 | Price et al. |
| 2011/0015660 | A1 | 1/2011 | Wiener et al. |
| 2012/0116265 | A1 | 5/2012 | Houser et al. |
| 2015/0080924 | A1 | 3/2015 | Stulen et al. |
| 2015/0141981 | A1 | 5/2015 | Price et al. |
| 2015/0164532 | A1* | 6/2015 | Faller ............ A61B 17/320092 606/169 |
| 2016/0143659 | A1 | 5/2016 | Glutz et al. |
| 2016/0213395 | A1* | 7/2016 | Anim .................... A61L 31/041 |
| 2019/0000499 | A1 | 1/2019 | Stokes et al. |

OTHER PUBLICATIONS

International Search Report and Written Opinion dated Jun. 18, 2020 for Application No. PCT/IB2020/053470, 11 pgs.

\* cited by examiner

ULTRASONIC BLADE AND CLAMP ARM MATCHING DESIGN

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; and U.S. Pat. No. 9,095,367, published Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
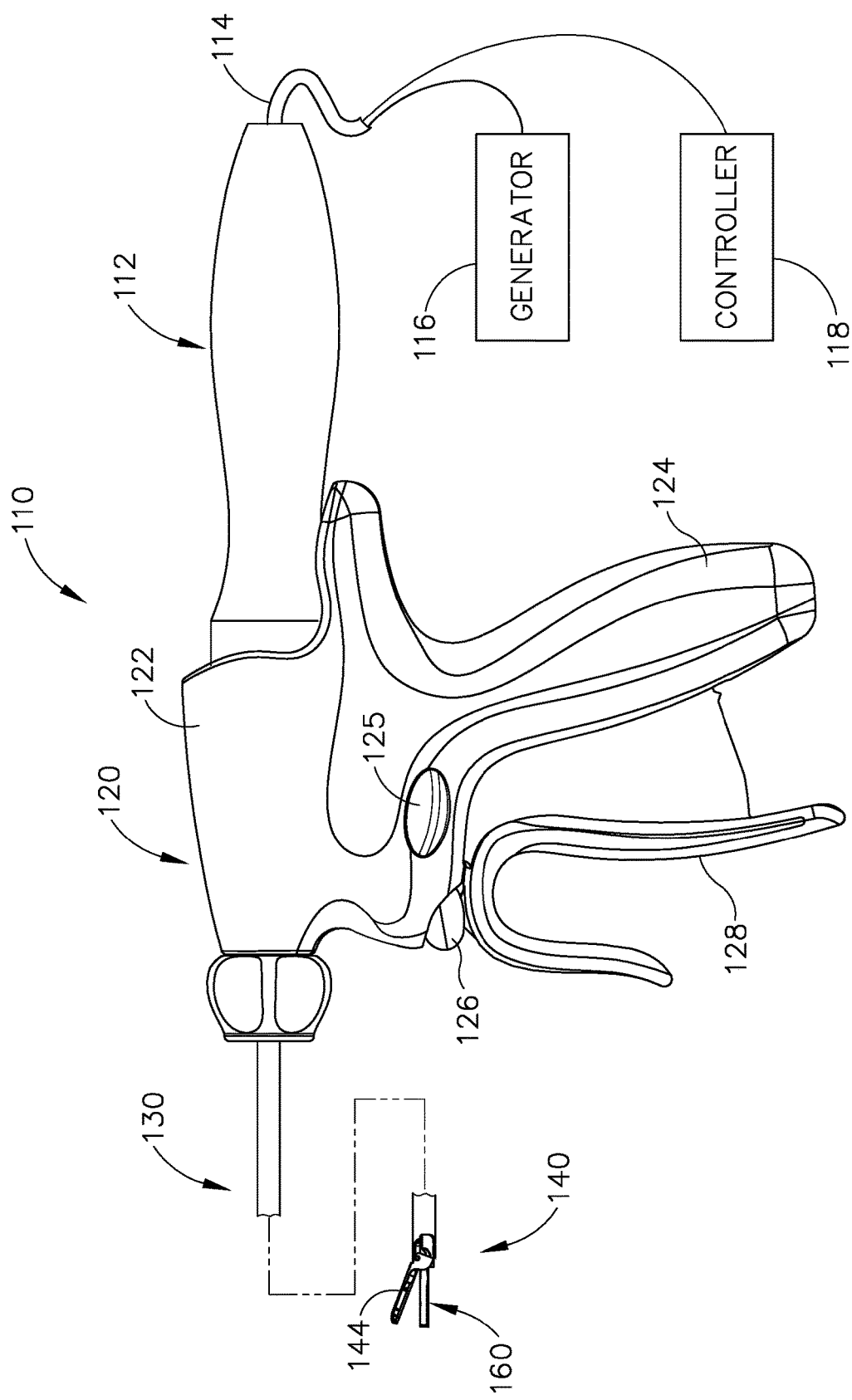
FIG. 1 depicts a side elevational view of a first exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates a first exemplary ultrasonic surgical instrument (110). At least part of instrument (110) may be constructed and operable in accordance with at least some of the teachings of any of the patent references that are cited herein. As described therein and as will be described in greater detail below, instrument (110) is operable to cut tissue and seal or weld tissue (e.g., a blood vessel, etc.) substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (125, 126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) are disclosed in various patent references cited herein; and further suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 1.

An ultrasonic transducer assembly (112) extends proximally from body (122) of handle assembly (120) in the present example. In some other versions, transducer assembly (112) is fully integrated within body (122). Transducer assembly (112) is coupled with a generator (116) via a cable (114). Transducer assembly (112) receives electrical power from generator (116) and converts that electrical power into ultrasonic vibrations through piezoelectric principles as is known in the art. Generator (116) cooperates with a controller (118) to provide a power profile to transducer assembly (112) that is particularly suited for the generation of ultrasonic vibrations through transducer assembly (112). While controller (118) is represented by a box that is separate from generator (116) in FIG. 1, controller (118) and generator (116) may be integrated together in a single unit. By way of example only, generator (116) may comprise a GEN04 or GEN11 sold by Ethicon Endo-Surgery, Inc. of Cincinnati, Ohio. In addition, or in the alternative, generator (116) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

End effector (140) of the present example comprises clamp arm (144) and ultrasonic blade (160). Clamp arm (144) includes a clamp pad (not shown) that is secured to the underside of clamp arm (144), facing blade (160). By way of example only, the clamp pad (not shown) may be formed of a polytetrafluoroethylene (PTFE) material and/or any other suitable material(s). By way of further example only, the clamp pad (not shown) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is operable to selectively pivot toward and away from blade (160) to selectively clamp tissue between clamp arm (144) and blade (160) in response to pivoting of trigger (128) toward pistol grip (124). Blade (160) of the present example is operable to vibrate at ultrasonic frequencies to effectively cut through and seal tissue, particularly when the tissue is being clamped between clamp arm (144) and blade (160). Blade (160) is positioned at the distal end of an acoustic drivetrain that includes an acoustic waveguide (not shown) and transducer assembly (112) to vibrate blade (160). By way of example only, the acoustic waveguide and blade (160) may comprise components sold under product codes SNGHK and SNGCB by Ethicon Endo-Surgery, Inc. of Cincinnati, Ohio. By way of further example only, the acoustic waveguide and blade (160) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the acoustic waveguide and blade (160) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations that may be used for the acoustic waveguide and blade (160) will be apparent to those of ordinary skill in the art in view of the teachings herein.

In the present example, the distal end of blade (160) is located at a position corresponding to an anti-node associated with resonant ultrasonic vibrations communicated through a flexible acoustic waveguide, to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. For instance, blade (160) and clamp arm (144) may be configured to apply radiofrequency (RF) electrosurgical energy to tissue in addition to being configured to apply ultrasonic energy to tissue.

Buttons (125, 126) may provide the operator with varied control of the instrument (110). In addition, or in the alternative, buttons (125, 126) may provide functionality in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. Other suitable ways in which buttons (125, 126) may provide operation of instrument (110) will be apparent to those of ordinary skill in the art in view of the teachings herein.

In some instances, it may be desirable to provide a version of instrument (110) that is formed by a combination of components that are disposable (e.g., configured for use in only one surgical procedure) and components that are reusable (e.g., configured for use in more than one surgical procedure, subject to reprocessing and sterilization, etc., between surgical procedures). By way of example only, the disposable and reusable components of a surgical instrument may be assembled together to form the surgical instrument before a surgical procedure, the assembled surgical instrument may then be used to perform the surgical procedure, and then the disposable and reusable components of the surgical instrument may be disassembled after the surgical procedure is complete. Providing a disposable/reusable dichotomy among surgical instrument components may provide a reduction in cost and overall waste as compared to conventional instrumentations that are provided as an entirely disposable unit.

Figure 2:
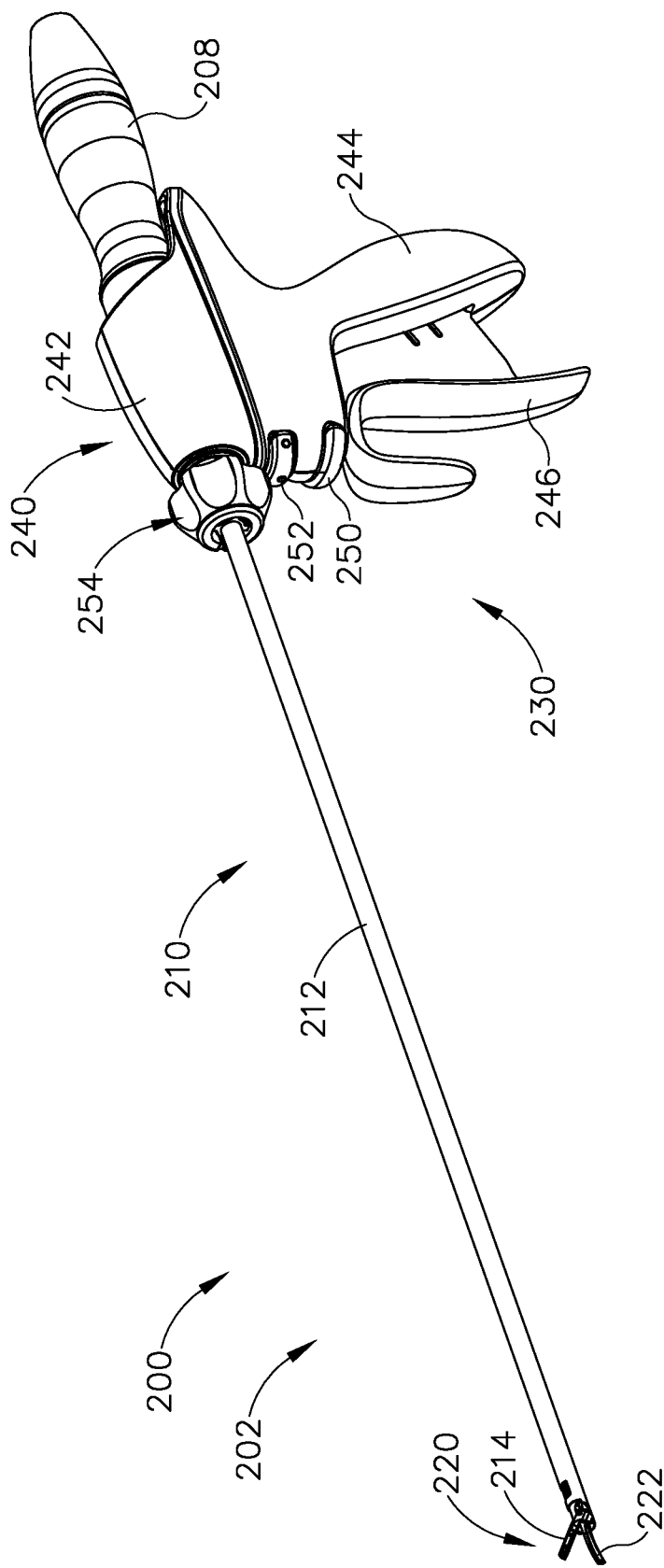
FIG. 2 depicts a perspective view of a second exemplary ultrasonic surgical instrument.
Figure 3:
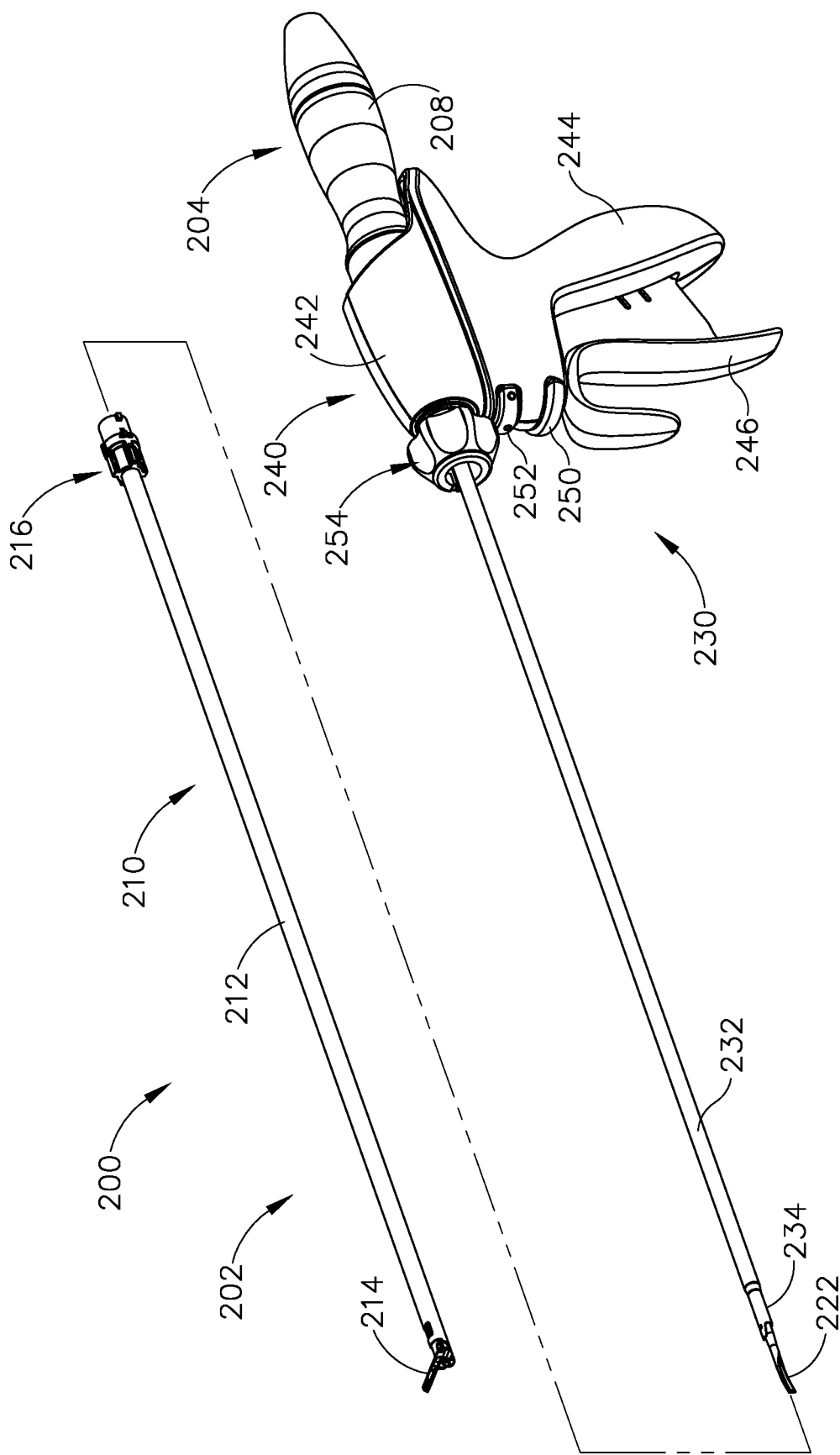
FIG. 3 depicts a partially exploded perspective view of the ultrasonic surgical instrument of FIG. 2.

II. Exemplary Ultrasonic Surgical Instrument with Pressure Distributing Clamp Pad FIGS. 2-3 show a second exemplary ultrasonic surgical instrument (200), similar to instrument (110). Except as otherwise described below, ultrasonic surgical instrument (200) may be configured and operable just like instrument (110) described above and/or in accordance with any of the various teachings of the various patent references cited herein. Surgical instrument (200) is configured to be readily broken down into disposable and reusable components. In particular, surgical instrument (200) of this example comprises a reusable assembly (204) and a partially disposable assembly (202). When fully assembled, surgical instrument (200) provides an end effector (220) that includes an ultrasonic blade (222) and a clamp arm (214), which is pivotable toward and away from ultrasonic blade (222). End effector (220) is thus operable to grasp, ultrasonically seal, and ultrasonically sever tissue as described herein and as described in various references cited herein. Clamp arm (214) is configured to distribute compression forces between clamp arm (214) and ultrasonic blade (222) as discussed below in greater detail.

Reusable assembly (204) comprises an ultrasonic transducer (208), which is operable to convert electrical power into ultrasonic vibrations, also as described herein and as described in various references cited herein. Ultrasonic transducer (208) is acoustically coupled with ultrasonic blade (222) via an acoustic waveguide (234), a portion of which is shown in FIG. 3. It should be understood that ultrasonic transducer (208), ultrasonic blade (222), and acoustic waveguide (234) may be configured in accordance with the teachings of any of the various references cited herein; or in any other suitable fashion.

Partially disposable assembly (202) of the present example comprises a disposable sub-assembly (210) and a reusable sub-assembly (230). Sub-assemblies (210, 230) are configured to be coupled together to form partially disposable assembly (202), which may then be coupled with reusable assembly (204) for form a complete ultrasonic surgical instrument (200). As shown in FIG. 3, disposable sub-assembly (210) comprises an outer tube (212). Clamp arm (214) is pivotally coupled with a distally projecting tongue of outer tube (212). A coupling member (216) is fixedly secured to the proximal end of outer tube (212). Disposable sub-assembly (210) further comprises a distal inner tube member (not shown), which is slidably and coaxially disposed within the distal end of outer tube (212). This distal inner tube member is also pivotally coupled with clamp arm (214) via a distally projecting tongue of the distal inner tube member. Thus, when outer tube (212) translates longitudinally relative to the distal inner tube member, clamp arm (214) will pivot toward and away from ultrasonic blade (222).

Reusable sub-assembly (230) of the present example comprises a handle assembly (240), a proximal inner tube member (232), acoustic waveguide (234), and ultrasonic blade (222). Proximal inner tube member (232) is configured to removably couple with the distal inner tube member of disposable sub-assembly (210) first when sub-assemblies (210, 230) are assembled together. When proximal inner tube member (232) is coupled with the distal inner tube member of disposable sub-assembly (210), inner tube members (232) remain longitudinally stationary relative to handle assembly (240).

Handle assembly (240) comprises a housing (242) that defines a pistol grip (244). Handle assembly (240) further includes a trigger (246) that is pivotable toward and away from pistol grip (244); and a pair of buttons (250, 252). Buttons (250, 252) are operable to activate ultrasonic transducer (208) to thereby activate ultrasonic blade (222). In particular, one button (250) will provide activation of ultrasonic blade (222) at one power level or profile; while the other button (252) will provide activation of ultrasonic blade (222) at another power level or profile. Of course, any other suitable user input feature(s) may be used.

Trigger (246) is operable to actuate clamp arm (214), such that clamp arm (214) will pivot toward ultrasonic blade (222) when trigger (246) us pivoted toward pistol grip (244); and such that clamp arm (214) will pivot away from ultrasonic blade (222) when trigger (246) us pivoted away from pistol grip (244). In the present example, this movement is provided by translating outer tube (212) longitudinally relative to housing (242) in response to pivotal movement of trigger (246), while inner tube members (232) remain longitudinally stationary relative to housing (242). Various suitable ways in which outer tube (212) may be translated longitudinally in response to pivotal movement of trigger (246) will be apparent to those of ordinary skill in the art in view of the teachings herein. It should also be understood that, in some alternative versions, clamp arm (214) is pivoted by translating inner tube members (232) longitudinally relative to housing (242) while outer tube (212) remains longitudinally stationary relative to housing (242).

As shown in FIGS. 2-3, handle assembly (240) of the present example further includes a knob member (254). Knob member (254) is rotatable relative to housing (242). When instrument (200) is fully assembled, knob member (254) is coupled with acoustic waveguide (234), inner tube members (232), and outer tube (212) such that these components will rotate together unitarily relative to housing (242). Knob member (254) also provides guidance to disposable sub-assembly (210) when disposable sub-assembly (210) is being coupled with reusable sub-assembly (230). By way of example only, knob member (254) may be configured and operable in accordance with the teachings of any of the various references cited herein.

After ultrasonic surgical instrument (200) is used in a surgical procedure, reusable assembly (204) may be removed from partially disposable assembly (202). After reusable assembly (204) is removed from partially disposable assembly (202), disposable sub-assembly (210) is then be removed from reusable sub-assembly (230). Reusable assembly (204), disposable sub-assembly (210), and reusable sub-assembly (230) may then be subject to different kinds of processing. Examples of such subsequent processing are described below, while other examples will be apparent to those of ordinary skill in the art in view of the teachings herein.

In some instances, reusable assembly (204) may be cleaned, sterilized, and re-used up to 100 times (by way of example only). Disposable sub-assembly (210) may be disposed of immediately, such that disposable sub-assembly (210) is only used in one single surgical procedure. Reusable sub-assembly (230) may be cleaned, sterilized, and re-used in different surgical procedures between 2 to 20 times (by way of example only). Of course, these re-use scenarios are merely illustrative examples. It should nevertheless be understood that the configuration of partially disposable assembly (202) may minimize the amount of single-use material that is disposed of after each surgical procedure. It should also be understood that, in some variations, partially disposable assembly (202) is simply disposed of as a single unit. In other words, in some variations, partially disposable assembly (202) is not configured to be disassembled into disposable sub-assembly (210) and reusable sub-assembly (230).

By way of example only, as part of the post-surgery processing for re-use, reusable assembly (204) and/or reusable sub-assembly (230) may be sterilized in a conventional relatively low temperature, relatively low pressure, hydrogen peroxide sterilization process (e.g., in a STERRAD® sterilizing system by Advanced Sterilization Products of Irvine, Calif.). Alternatively, reusable assembly (204) and/or reusable sub-assembly (230) may be sterilized using any other suitable systems and techniques.

In addition to the foregoing, instrument (200) may be constructed and operable in accordance with at least some of the teachings of U.S. patent application Ser. No. 15/270,540, entitled "Ultrasonic Surgical Instrument with Removable Shaft Assembly Portion," filed Sep. 20, 2016, issued as U.S. Pat. No. 10,327,797 on Jun. 25, 2019 the disclosure of which is incorporated by reference herein; and/or U.S. patent application Ser. No. 15/270,600, entitled "Ultrasonic Surgical Instrument with Removable Shaft Assembly Portion," filed Sep. 20, 2016, issued as U.S. Pat. No. 10,492,820 on Dec. 3, 2019, the disclosure of which is incorporated by reference herein. In addition, or in the alternative, instrument (200) may be constructed and operable in accordance with at least some of the teachings of any of the various patent references cited herein.

While clamp arm (214) may be fitted with the clamp pad (not shown) similar to clamp arm (144) (see FIG. 1) discussed above in greater detail for compressing tissue against ultrasonic blade (160) (see FIG. 1), such clamp pads (not shown) offer relatively little to no distribution of localized compression forces along the clamp pad (not shown) between clamp arm (144) (see FIG. 1) and ultrasonic blade (160) (see FIG. 1). For example, inconsistent tissue thicknesses, variable gaps between clamp arm (144) (see FIG. 1) and ultrasonic blade (160) (see FIG. 1), and/or differing blade vibrations between nodes and anti-nodes along ultrasonic blade (160) (see FIG. 1) tend to cause varying compression forces along ultrasonic blade (160) (see FIG. 1) or ultrasonic blade (222) that may inadvertently damage tissue, prematurely wear components, or cause inconsistencies while cutting and/or sealing tissue. It may thus be desirable in some instances to provide clamp arm (214) with such a clamp pad (260, 360, 460, 560) configured to distribute compression forces between clamp arm (214) and ultrasonic blade (222) for reducing the likelihood of such damage, wear, or inconsistencies as discussed below with respect to FIGS. 4A-11.

A. End Effector and First Exemplary Clamp Pad for Compression Distribution

Figure 4A:
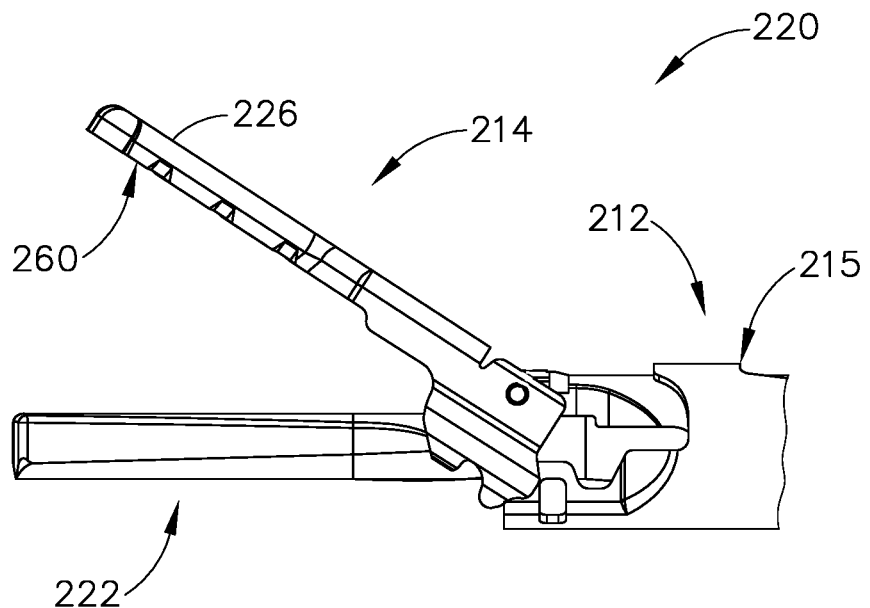
FIG. 4A depicts a side elevational view of an end effector of the ultrasonic instrument of FIG. 2 in an open configuration.
Figure 4B:
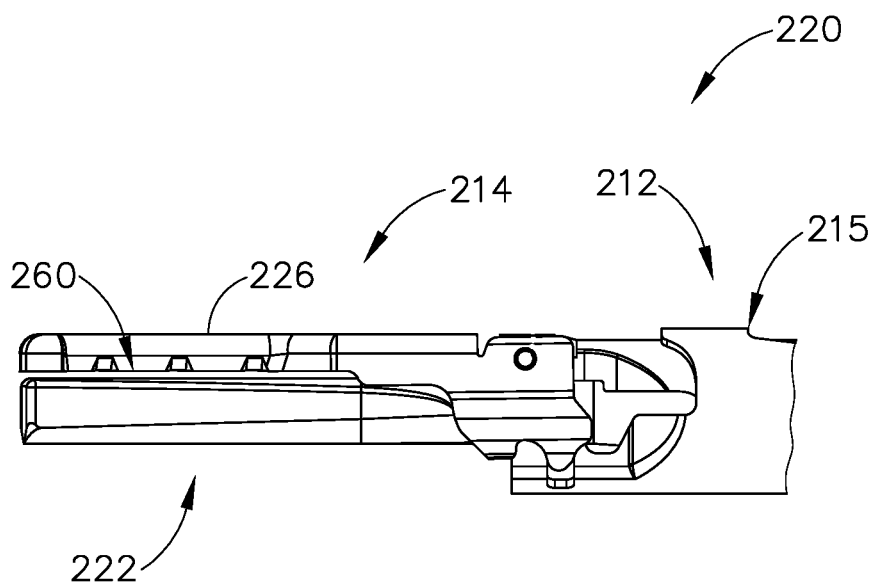
FIG. 4B depicts the side elevational view of the end effector of the ultrasonic instrument similar to FIG. 4A, but shown in a closed configuration.
Figure 5:
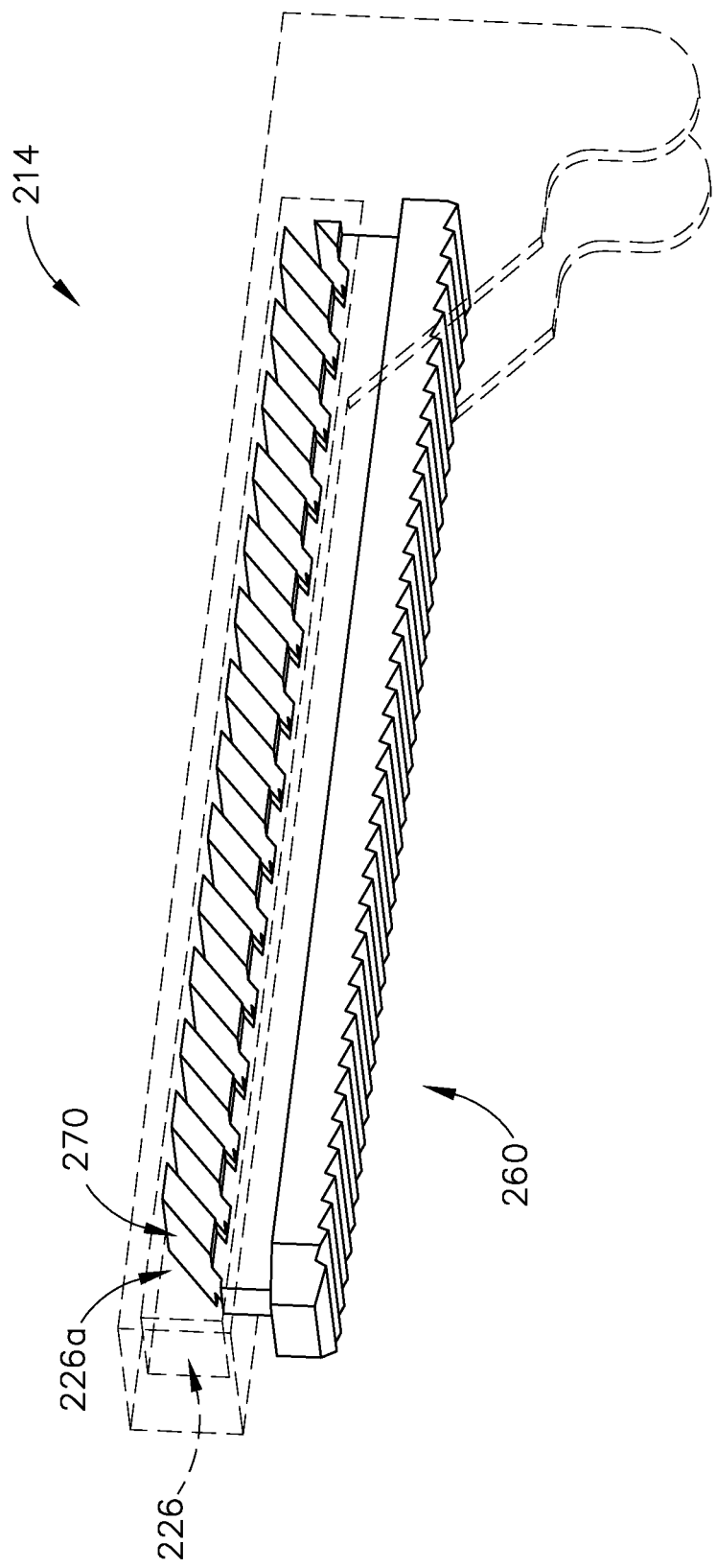
FIG. 5 depicts a schematic, perspective view of a clamp arm of the ultrasonic instrument of FIG. 2 having a first exemplary clamp pad.

With respect to FIGS. 4A-5, end effector (220) is coupled to outer tube (212) of instrument (200) (see FIG. 3) and distally extends from a portion of a shaft assembly (215). By way of further example, end effector (220) may be constructed and operable in accordance with end effector (140) of ultrasonic surgical instrument (110) except for such differences as otherwise provided below. End effector (220) comprises clamp arm (214) and ultrasonic blade (222), clamp arm (214) being configured to pivot toward ultrasonic blade (222) and clamp tissue therebetween. Clamp arm (214) is movably secured relative to ultrasonic blade (222) and has a mortise (226) which extends longitudinally therethrough that receives a first exemplary clamp pad (260) coupled to clamp arm (214). Clamp pad (260) has a predetermined transverse spring rate configured to equalize pressure upon compression against tissue toward ultrasonic blade (222) for distributing compression forces between clamp arm (214) and ultrasonic blade (222) during use. While such distribution of compression forces is thereby controlled to equalize pressure between clamp arm (214) and ultrasonic blade (222) in the present example of clamp pad (260), an alternative clamp pad (not shown) may be configured to distribute compression forces according to an alternative distribution of pressure as desired.

FIG. 4A shows end effector (220) in an open configuration such that clamp arm (214) is positioned away from ultrasonic blade (222). In this position of the present example, no pressure is applied to clamp arm (214) by ultrasonic blade (222) through the clamped tissue (not shown). FIG. 4B shows end effector (220) in a closed configuration such that clamp arm (214) is pivoted toward ultrasonic blade (222) to apply pressure to clamp arm (214) by ultrasonic blade (222) through the clamped tissue (not shown). FIG. 5 shows a tenon (270) of clamp pad (260) seated within mortise (226) to removably secure clamp pad (260) to clamp arm (214).

Figure 6:
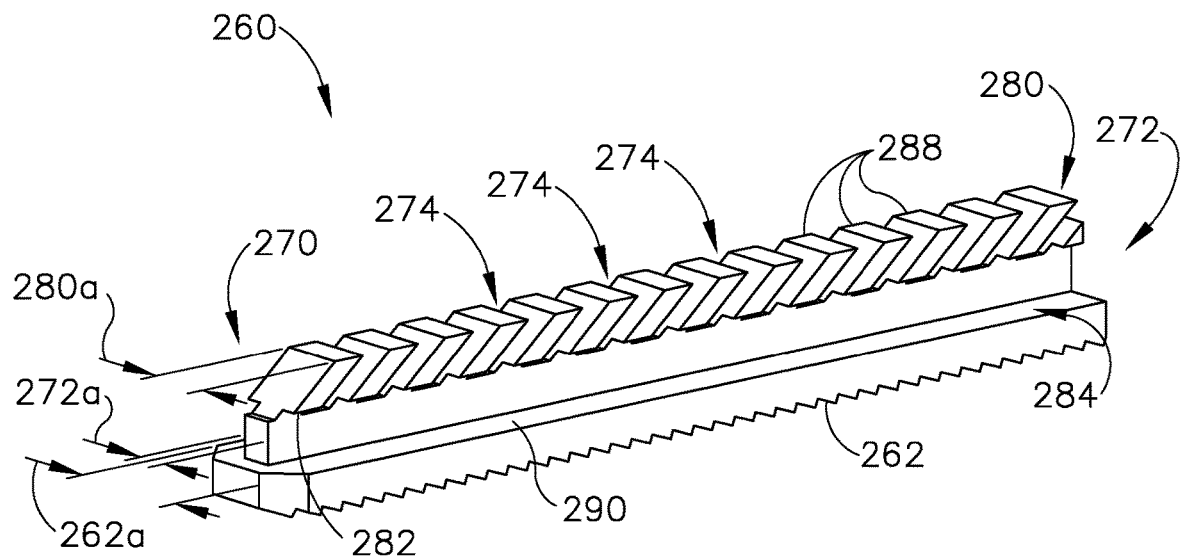
FIG. 6 depicts a perspective view of the clamp pad of FIG. 5.

With respect to FIG. 6, clamp pad (260) more particularly includes tenon (270) and a pad body (262). Pad body (262) extends in a longitudinal direction and is configured to directly engage tissue, although it will be appreciated that pad body (262) may extend in any desired direction to align with ultrasonic blade (222) (see FIG. 4A). Pad body (262) of the present example extends distally beyond tenon (270) such that the distal end of pad body (262) terminates at a position relatively distal from the distal end of tenon (270). Tenon (270) is secured to pad body (262) and received within mortise (226) (see FIG. 5) of clamp arm (214) (see FIG. 5). In the present example, tenon (270) includes a rail (272), a support base (280), and a plurality of openings (274). Rail (272) extends in a transverse direction, upward from pad body (262) as shown in FIG. 6 and has a first lateral width (272a) in a lateral direction perpendicular to the longitudinal and transverse directions. Support base (280) extends in the transverse direction from rail (272) and has a second lateral width (280a) in the lateral direction. Second lateral width (280a) of support base (280) is larger than first lateral width (272a) of rail (272) such that support base (280) with second lateral width (280a) defines a shoulder (282) configured to transversely engage clamp arm (214) (see FIG. 5) and secure pad body (262) to clamp arm (214) (see FIG. 5). Each opening (274) extends through support base (280) such that tenon (270) has the predetermined transverse spring rate longitudinally along tenon (270) from a distal end to a proximal end thereof. The predetermined transverse spring rate of tenon (270) is thus configured to distribute pressure longitudinally along pad body (262) when pad body (262) is compressed against the tissue and equalize pressure therealong for reducing localized compression forces. Alternatively, the predetermined transverse spring rate according to another example may be configured to distribute pressure to a generate a non-uniform, controlled distribution of force longitudinally along pad body (262) as desired. In the present example, rail (272), support base (280) and pad body (262) are unitarily formed, although it will be appreciated that rail (272), support base (280), and/or pad body (262) may alternatively be one or more respective discretely formed portions fastened together in other examples.

With openings (274) in support base (280), the present exemplary support base (280) is defined by a plurality of resilient base members (288) projecting in the transverse direction from rail (272). Resilient base members (288) of FIG. 6 are arranged in a longitudinal row of resilient base members (288) spaced apart from each other to respectively define openings (274) therebetween. In the present example, openings (274) extend through support base (280) in the lateral, longitudinal, and transverse directions. More particularly, openings (274) extend completely through support base (280) an entire second lateral width (280a) in the lateral direction.

Resilient base members (288) of the present example are generally rectangular, have uniform dimensions, and do not contact each other except as connected by rail (272). Each resilient base member (288) projects in the transverse direction and proximally in the longitudinal direction at a predetermined pitch relative to pad body (262). Resilient base members (288) are seated against a bottom (226a) (see FIG. 5) of mortise (226) (see FIG. 5) and configured to resiliently deflect independent of each other and toward pad body (262) according to the predetermined transverse spring rate in the transverse and longitudinal directions. The predetermined pitch may be in any angle as desired to achieve any desired predetermined transverse spring rate. In the present example, the predetermined pitch is constant along the longitudinal length of support base (280) such that each resilient base member (288) has the same predetermined pitch. Alternatively, another example of a predetermined pitch may be a variable predetermined pitch along the longitudinal length of support base (280) such that one or more resilient base members (288) may have different, varying predetermined pitches. Support base (280) shown in FIG. 6 has fourteen resilient base members (288), although it will be appreciated that any number of resilient base members (288) may be so used for defining support base (280). Such uniformity of resilient base members (288) is configured to distribute forces equally along support base (280) in the present example, but alternative base members (not shown) may be non-uniform in another example to thereby generate a non-uniform, controlled distribution of force as desired. In addition, the predetermined pitch of resilient base members (288) is further configured to generate a reactionary force under compression to urge pad body (262) distally in the longitudinal direction for further securing clamp pad (260) in mortise (226a) (see FIG. 5).

Furthermore, clamp pad (260) has an overload surface (284) configured to inhibit localized deflection should a localized portion pad body (262) effectively "bottom-out" from being overly compressed. For example, base members (288) are configured to deflect when compressed against bottom (226a) (see FIG. 5) of mortise (226a) (see FIG. 5) toward pad body (262) from an uncompressed position to a fully compressed position. Once in the fully compressed position, overload surface (284) engages with clamp arm (214) to bottom-out, thus arresting further localized transverse compression of base members (288) and inhibit further deflection thereof. In one example, clamp pad (260) is resilient, but has a higher spring rate than support base (280) such that pad body (262) may continue to deflect to some extent, but with little to no distribution of compression forces along pad body (262). As shown in FIG. 6, overload surface (284) is on another shoulder (290) defined by a third lateral width (262a) of pad body (262) being larger than first lateral width (272a) of rail (272). Overload surface (284) may be alternatively positioned in another example to engage with another portion of clamp arm (214) (see FIG. 5) such that the invention is not intended to be unnecessarily limited to overload surface (284) shown in the present example.

B. Second Exemplary Clamp Pad for Compression Distribution

Figure 7:
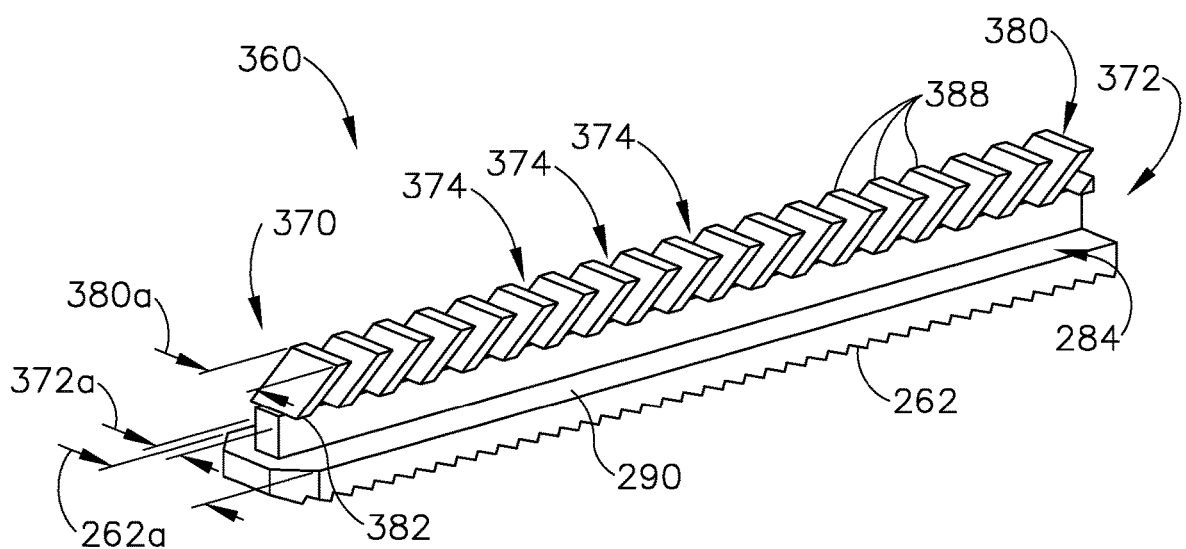
FIG. 7 depicts a perspective view of a second exemplary clamp pad.

FIG. 7 shows a second exemplary clamp pad (360) having a tenon (370) extending from pad body (262), which is discussed above in greater detail. Tenon (370) is secured to pad body (262) and received within mortise (226) (see FIG. 5) of clamp arm (214) (see FIG. 5). In the present example, tenon (370) includes a rail (372), a support base (380), and a plurality of openings (374). Rail (372) extends in a transverse direction, upward from pad body (262) as shown in FIG. 7, and has a first lateral width (372a) in a lateral direction perpendicular to the longitudinal and transverse directions. Support base (380) extends in the transverse direction from rail (372) and has a second lateral width (380a) in the lateral direction. Second lateral width (380a) of support base (380) is larger than first lateral width (372a) of rail (372) such that support base (380) with second lateral width (380a) defines a shoulder (382) configured to transversely engage clamp arm (214) (see FIG. 5) and secure pad body (262) to clamp arm (214) (see FIG. 5). Each opening (374) extends through support base (380) such that tenon (370) has a predetermined transverse spring rate longitudinally along tenon (370) from a distal end to a proximal end thereof. The predetermined transverse spring rate of tenon (370) is thus configured to distribute pressure longitudinally along pad body (262) when pad body (262) is compressed against the tissue and equalize pressure therealong for reducing localized compression forces. While such distribution of compression forces is thereby controlled to equalize pressure between clamp arm (214) (see FIG. 5) and ultrasonic blade (222) (see FIG. 4A) in the present example of clamp pad (360), an alternative clamp pad (not shown) may be configured to distribute compression forces according to an alternative distribution of pressure as desired. For example, the predetermined transverse spring rate according to another example may be configured to distribute pressure to a generate a non-uniform, controlled distribution of force longitudinally along pad body (262) as desired. In the present example, rail (372), support base (380) and pad body (262) are unitarily formed, although it will be appreciated that rail (372), support base (380), and/or pad body (262) may alternatively be one or more respective discretely formed portions fastened together in other examples.

With openings (374) in support base (380), the present exemplary support base (380) is defined by a plurality of resilient base members (388) projecting in the transverse direction from rail (372). Resilient base members (388) of FIG. 7 are arranged in a longitudinal row of resilient base members (388) spaced apart from each other to respectively define openings (374) therebetween. In the present example, openings (374) extend through support base (380) in the lateral, longitudinal, and transverse directions. More particularly, openings (374) extend completely through support base (380) an entire second lateral width (380a) in the lateral direction.

Resilient base members (388) of the present example are generally rectangular, have uniform dimensions, and do not contact each other except as connected by rail (372). Each resilient base member (388) projects in the transverse direction and proximally in the longitudinal direction at a predetermined pitch relative to pad body (262). Resilient base members (388) are seated against bottom (226a) (see FIG. 5) of mortise (226) (see FIG. 5) and configured to resiliently deflect independent of each other and toward pad body (262) according to the predetermined transverse spring rate in the transverse and longitudinal directions. The predetermined pitch may be in any angle as desired to achieve any desired predetermined transverse spring rate. In the present example, the predetermined pitch is constant along the longitudinal length of support base (380) such that each resilient base member (388) has the same predetermined pitch. Alternatively, another example of a predetermined pitch may be a variable predetermined pitch along the longitudinal length of support base (380) such that one or more resilient base members (388) may have different, varying predetermined pitches. Support base (380) shown in FIG. 7 has nineteen resilient base members (388), although it will be appreciated that any number of resilient base members (388) may be so used for defining support base (380). Such uniformity of resilient base members (388) is configured to distribute forces equally along support base (380) in the present example, but alternative base members (not shown) may be non-uniform in another example to thereby generate a non-uniform, controlled distribution of force as desired. Each resilient base member (388) has second lateral width (380a) in the lateral direction, and the predetermined pitch of resilient base members (388) is further configured to generate a reactionary force under compression to urge pad body (262) distally in the longitudinal direction for further securing clamp pad (360) in mortise (226) (see FIG. 5). In addition, pad body (262) of clamp pad (360) further includes overload surface (284) on shoulder (290) for arresting localized transverse compression of base members (388) in use.

C. Third Exemplary Clamp Pad for Compression Distribution

Figure 8:
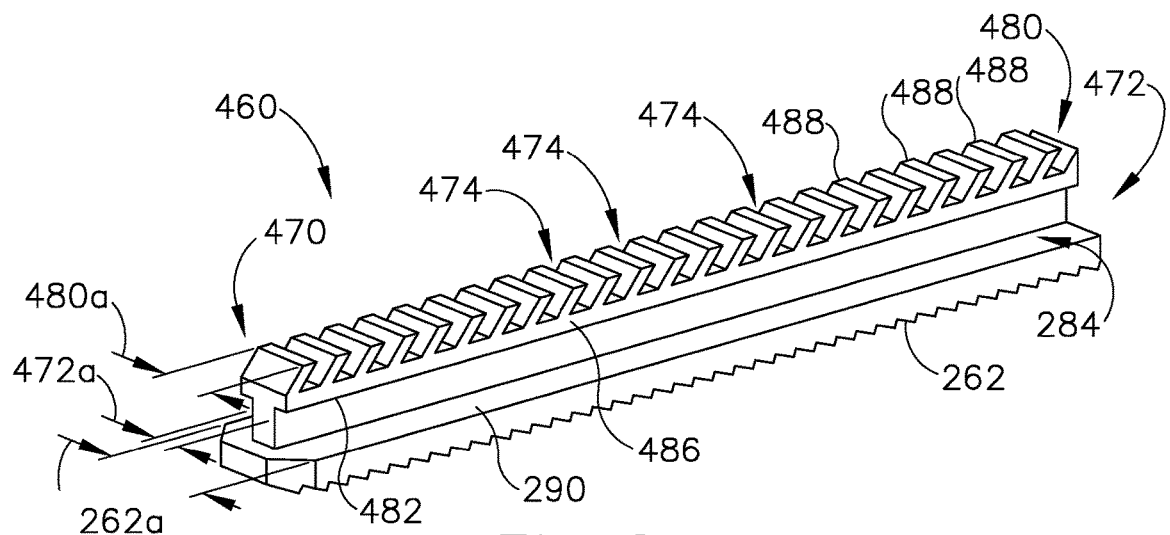
FIG. 8 depicts a perspective view of a third exemplary clamp pad.

FIG. 8 shows a third exemplary clamp pad (460) having a tenon (470) extending from pad body (262), which is discussed above in greater detail. Tenon (470) is secured to pad body (262) and received within mortise (226) (see FIG. 5) of clamp arm (214) (see FIG. 5). In the present example, tenon (470) includes a rail (472), a support base (480), and a plurality of openings (474). Rail (472) extends in a transverse direction, upward from pad body (262) as shown in FIG. 8 and has a first lateral width (472a) in a lateral direction perpendicular to the longitudinal and transverse directions. Support base (480) extends in the transverse direction from rail (472) and has a second lateral width (480a) in the lateral direction. Second lateral width (480a) of support base (480) is larger than first lateral width (472a) of rail (472) such that support base (480) with second lateral width (480a) defines a shoulder (482) configured to transversely engage clamp arm (214) (see FIG. 5) and secure pad body (262) to clamp arm (214) (see FIG. 5). Each opening (474) extends through support base (480) such that tenon (470) has a predetermined transverse spring rate longitudinally along tenon (470) from a distal end to a proximal end thereof. The predetermined transverse spring rate of tenon (470) is thus configured to distribute pressure longitudinally along pad body (262) when pad body (262) is compressed against the tissue and equalize pressure therealong for reducing localized compression forces. While such distribution of compression forces is thereby controlled to equalize pressure between clamp arm (214) (see FIG. 5) and ultrasonic blade (222) (see FIG. 4A) in the present example of clamp pad (460), an alternative clamp pad (not shown) may be configured to distribute compression forces according to an alternative distribution of pressure as desired. For example, the predetermined transverse spring rate according to another example may be configured to distribute pressure to a generate a non-uniform, controlled distribution of force longitudinally along pad body (262) as desired. In the present example, rail (472), support base (480) and pad body (262) are unitarily formed, although it will be appreciated that rail (472), support base (480), and/or pad body (262) may alternatively be one or more respective discretely formed portions fastened together in other examples.

With openings (474) in support base (480), the present exemplary support base (480) is defined by a plurality of resilient base members (488) projecting in the transverse direction from rail (472). Resilient base members (488) are further coupled by a buttress member (486), such that buttress member (486) laterally extends second lateral width (480a) and transversely extends between resilient base members (488) and rail (472) of tenon (470). Resilient base members (488) of FIG. 8 are arranged in a longitudinal row of resilient base members (488) spaced apart from each other to respectively define openings (474) therebetween. In the present example, openings (474) extend through support base (480) in the lateral, longitudinal, and transverse directions. More particularly, openings (474) extend completely through support base (480) an entire second lateral width (480a) in the lateral direction.

Resilient base members (488) of the present example are generally rectangular, have uniform dimensions, and do not contact each other except as connected by rail (472). Each resilient base member (488) projects in the transverse direction and proximally in the longitudinal direction at a predetermined pitch relative to pad body (262) from buttress member (486). Resilient base members (488) are seated against bottom (226a) (see FIG. 5) of mortise (226) (see FIG. 5) and configured to resiliently deflect independent of each other and toward pad body (262) according to the predetermined transverse spring rate in the transverse and longitudinal directions. The predetermined pitch may be in any angle as desired to achieve any desired predetermined transverse spring rate. In the present example, the predetermined pitch is constant along the longitudinal length of support base (480) such that each resilient base member (488) has the same predetermined pitch. Alternatively, another example of a predetermined pitch may be a variable predetermined pitch along the longitudinal length of support base (480) such that one or more resilient base members (488) may have different, varying predetermined pitches. Support base (480) shown in FIG. 8 has twenty-three resilient base members (488), although it will be appreciated that any number of resilient base members (488) may be so used for defining support base (480). Such uniformity of resilient base members (488) is configured to distribute forces equally along support base (480) in the present example, but alternative base members (not shown) may be non-uniform in another example to thereby generate a non-uniform, controlled distribution of force as desired. Each resilient base member (488) has a second lateral width (480a) in the lateral direction. In addition, pad body (262) of clamp pad (460) further includes overload surface (284) on shoulder (290) for arresting localized transverse compression of base members (488).

D. Fourth Exemplary Clamp Pad for Compression Distribution

Figure 9:
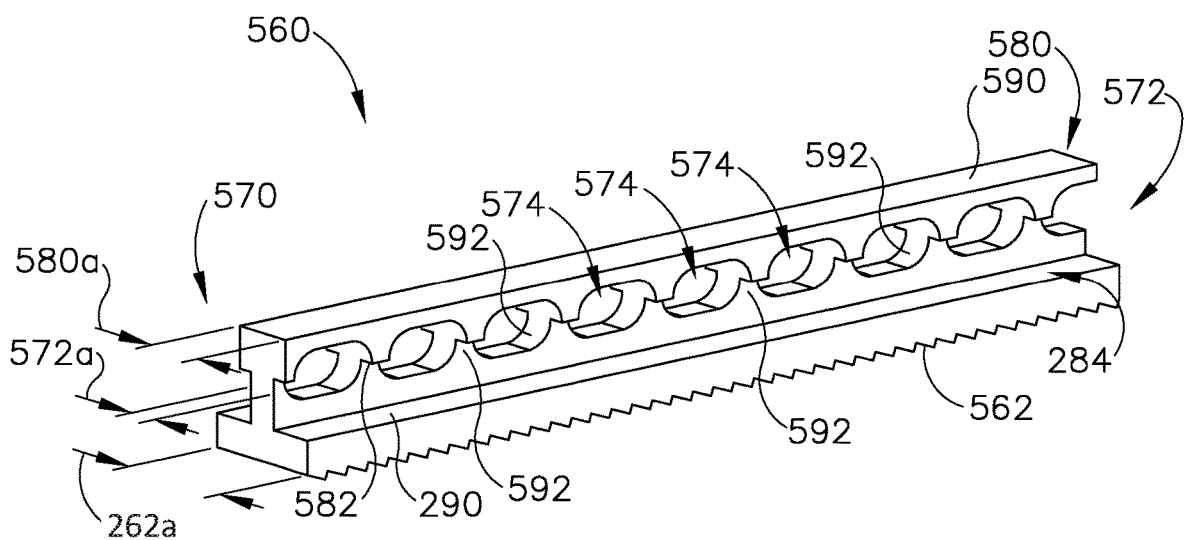
FIG. 9 depicts a perspective view of a fourth exemplary clamp pad.

FIG. 9 shows a fourth exemplary clamp pad (560) having a tenon (570) extending from pad body (562), which is similar to pad body (262) (see FIG. 6) discussed above in greater detail, but distally terminates adjacent to tenon (570) such that the distal end of pad body (262) is co-planar with the distal end of tenon (570). Tenon (570) is secured to pad body (562) and received within mortise (226) (see FIG. 5) of clamp arm (214) (see FIG. 5). In the present example, tenon (570) includes a rail (572), a support base (580), and a plurality of openings (574). Rail (572) extends in a transverse direction, upward from pad body (562) as shown in FIG. 9, and has a first lateral width (572a) in a lateral direction perpendicular to the longitudinal and transverse directions. Support base (580) extends in the transverse direction from rail (572) and has a second lateral width (580a) in the lateral direction. Second lateral width (580a) of support base (580) is larger than first lateral width (572a) of rail (572) such that support base (580) with second lateral width (580a) defines a shoulder (582) configured to transversely engage clamp arm (214) (see FIG. 5) and secure pad body (562) to clamp arm (214) (see FIG. 5). Each opening (574) extends through portions of support base (580) and rail (572) such that tenon (570) has the predetermined transverse spring rate longitudinally along tenon (570) from a distal end to a proximal end thereof. The predetermined transverse spring rate of tenon (570) is thus configured to distribute pressure longitudinally along pad body (562) when pad body (562) is compressed against the tissue and equalize pressure therealong for reducing localized compression forces. While such distribution of compression forces is thereby controlled to equalize pressure between clamp arm (214) (see FIG. 5) and ultrasonic blade (222) (see FIG. 4A) in the present example of clamp pad (560), an alternative clamp pad (not shown) may be configured to distribute compression forces according to an alternative distribution of pressure as desired. For example, the predetermined transverse spring rate according to another example may be configured to distribute pressure to a generate a non-uniform, controlled distribution of force longitudinally along pad body (562) as desired. In the present example, rail (572), support base (580) and pad body (562) are unitarily formed, although it will be appreciated that rail (572), support base (580), and/or pad body (562) may alternatively be one or more respective discretely formed portions fastened together in other examples.

With openings (574) in support base (580), the present exemplary support base (580) is defined by an elongate support member (590) extending in the longitudinal direction and a plurality of pier members (592) transversely extending between rail (572) and elongate support member (590). Each opening (574) laterally extends through support base (580) and rail (572) respectively between pier members (592). More particularly, openings (574) extend completely through support base (580) an entire second lateral width (580a) and also through rail (572) an entire first lateral width (572a) in the lateral direction.

Elongate support member (590) of the present example is generally rectangular in length is continuous except as passed through by openings (574). Piers (592) are generally T-shaped in the present example and have uniform dimensions along elongate support member (590). Elongate support member (590) is seated against a bottom (226a) (see FIG. 5) of mortise (226) (see FIG. 5) as well as piers (592) are configured to resiliently deflect toward pad body (562) according to the predetermined transverse spring rate in the transverse and longitudinal directions. Piers (592), which transversely extend from elongate support member (590) toward pad body (562), have a predetermined pitch further configured to generate the predetermined transverse spring rate. In the present example, the predetermined pitch in the transverse direction, perpendicular to the lateral and longitudinal directions, although the predetermined pitch may be in any angle as desired to achieve any desired predetermined transverse spring rate. In the present example, the predetermined pitch is constant along the longitudinal length of support base (580) such that each pier (592) has the same predetermined pitch. Alternatively, another example of a predetermined pitch may be a variable predetermined pitch along the longitudinal length of support base (580) such that one or more piers (580) may have different, varying predetermined pitches. Support base (580) shown in FIG. 9 has one elongate support member (590) and nine piers (592), although it will be appreciated that any number of elongate support members (590) and/or piers (592) may be so used for defining support base (580). Such uniformity of piers (592) is configured to distribute forces equally along support base (580) in the present example, but alternative piers (not shown) may be non-uniform in another example to thereby generate a non-uniform, controlled distribution of force as desired. In addition, pad body (562) of clamp pad (560) further includes overload surface (284) on shoulder (290) for arresting localized transverse compression of elongate support members (590) and piers (592).

III. Exemplary Ultrasonic Surgical Instrument with Self Balance Clamp Arm

Figure 10:
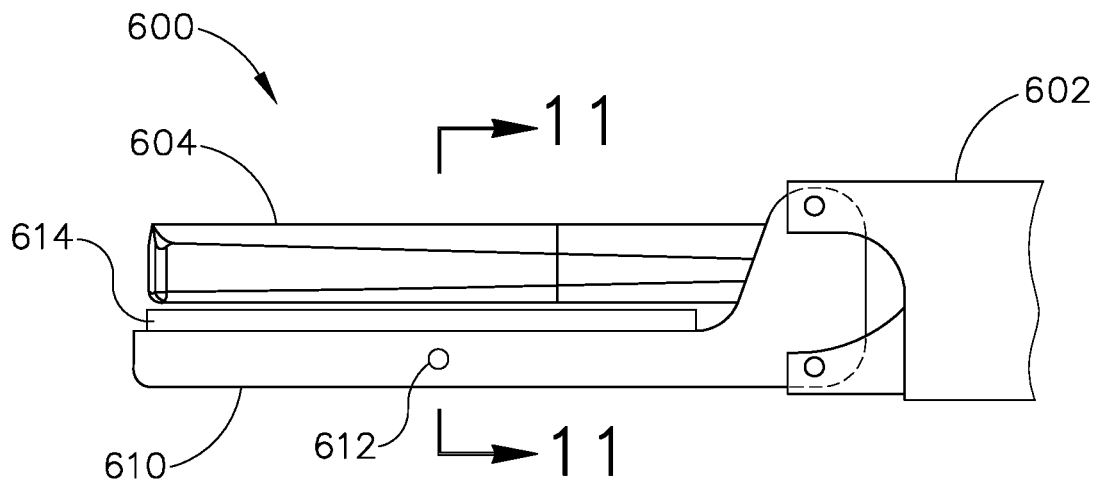
FIG. 10 depicts a schematic, side elevational view of an alternative example of an end effector configured to self-balance.
Figure 11:
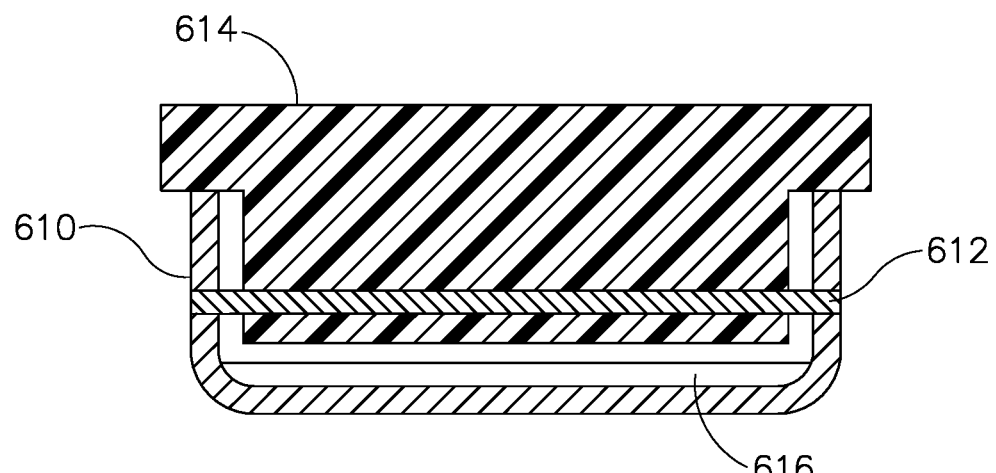
FIG. 11 depicts a schematic, cross-sectional view of the end effector of FIG. 10 taken along section line 11-11 of FIG. 10.

FIG. 10 illustrates an alternative example of an end effector (600) configured for use with an instrument such as ultrasonic surgical instrument (110) (see FIG. 1) or ultrasonic surgical instrument (200) (see FIG. 2). End effector (600) extends distally from elongate shaft (602) and comprises ultrasonic blade (604) and clamp arm (610). Clamp arm (610) comprises balance pin (612), which passes though the lateral width of clamp arm (610) and tissue pad (614) to clamp arm (610). As shown, ultrasonic blade (604) extends relative to elongate shaft (602) such that clamp arm (610) is configured to pivot between a first position away from ultrasonic blade (604) and a second position in contact with ultrasonic blade (604). With respect to FIG. 11, balance pin (612) passes through clamp arm (610) and tissue pad (614). Tissue pad (614) is configured to pivot on balance pin (612), and balance pin (612) holds tissue pad (614) in place. Balance pin (612) further serves as a retention pin for tissue pad (612), which reduces the use of other, more complex retention features on clamp arm (610), and, in some embodiments, may be welded in place. Further, elastomer (616) is over-molded to clamp arm (610) where tissue pad (614) rests above elastomer (616), and where tissue pad (614) contacts elastomer (616) as it pivots. Elastomer (616) may be a low durometer elastomer material, PTFE, or other suitable material.

Figure 12:
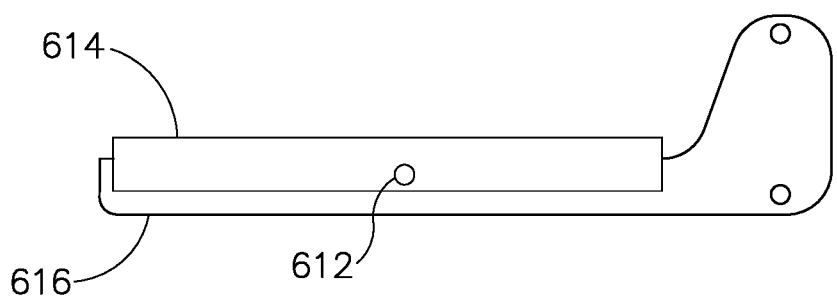
FIG. 12 depicts a schematic side elevational view of the end effector of FIG. 10 in an uncompressed state.
Figure 13:
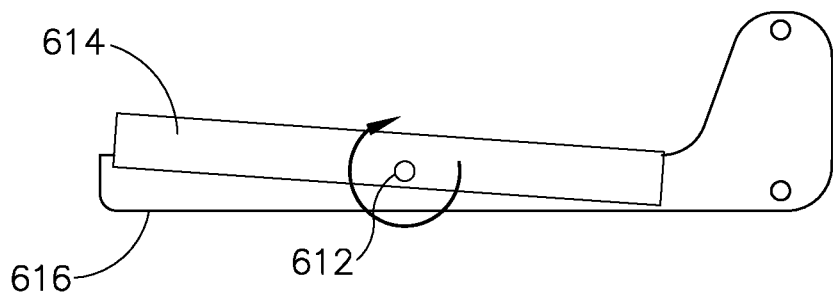
FIG. 13 depicts a side elevational view of the end effector of FIG. 10 in a first compressed state.
Figure 14:
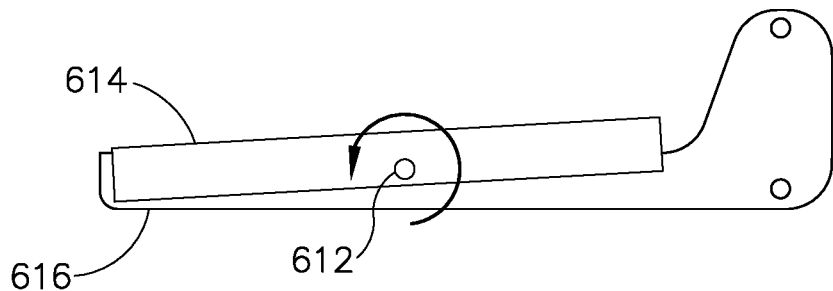
FIG. 14 depicts a side elevational view of the end effector of FIG. 10 in a second compressed state.

Referring now to FIGS. 12-14, clamp arm (610) is shown in configurations wherein clamp arm (610) will self-balance while under a load. It is contemplated that as ultrasonic blade (604) rotates on balance pin (612) toward clamp arm (610) and compresses tissue pad (614), tissue pad (614) will compress elastomer (616). FIG. 12 illustrates clamp arm (610) with no compression or load such that tissue pad (614) remains balanced. For proximally loaded compression, tissue pad (614) will compress more proximal causing tissue pad (614) to pivot clockwise, putting more pressure at distal end of tissue pad (614) as shown in FIG. 13. The opposite occurrence is disclosed in FIG. 14 wherein tissue pad (614) pivots counterclockwise. Alternatively, compression may be relatively balanced between distal end proximal portions such that tissue pad (614) undergoes little to no pivoting as previously shown in FIG. 12.

Figure 15:
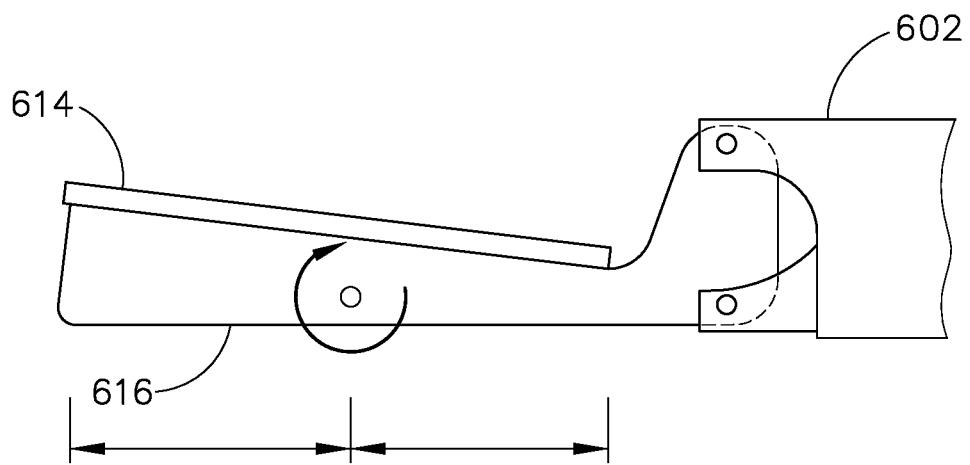
FIG. 15 depicts a side elevational view of the end effector of FIG. 10 in a compressed state with an ultrasonic blade deflected for aligned engagement toward a clamp arm.

Use of self-balancing tissue pad (614) pivoting on balance pin (612) further reduces the probability of a tip gap on end effectors (600). As shown with the present end effector (600) of FIG. 15 comprising balance pin (612), any tip gap is reduced as tissue pad (614) is configured to rotate and balance the load applied to elastomer (616) and clamp arm (610). The reduction of the probability of tip gap additionally removes the necessity of burn in during manufacture. Further, as illustrated with FIG. 15, the sensitivity of self-balancing clamp arm (610) can be tuned by changing the ratio of length L1 distal of balance pin (612) and length L2 proximal of balance pin (612). A higher sensitivity can be achieved when L2 is greater than L1, and a lower sensitivity can be achieved when L1 is greater than L2.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a shaft assembly; and (b) an end effector extending distally from the shaft assembly and including; (i) an ultrasonic blade, (ii) a clamp arm movably secured relative to the ultrasonic blade and having a mortise longitudinally extending therethrough, and (iii) a clamp pad connected to the clamp arm, including: (A) a pad body extending in a longitudinal direction and configured to compress a tissue toward the ultrasonic blade; and (B) a tenon secured to the pad body and received within the mortise, the tenon including: (I) a rail extending in a transverse direction from the pad body and having a first lateral width in a lateral direction perpendicular to the longitudinal and transverse directions, (II) a support base extending in the transverse direction from the rail and having a second lateral width in the lateral direction, wherein the second lateral width is larger width is larger than the first lateral width to define a first shoulder configured to engage the clamp arm for securement within the clamp arm, and (III) a plurality of openings extending through at least one of the support base or the rail such that the tenon has a predetermined transverse spring rate longitudinally along the tenon, wherein the predetermined transverse spring rate of the tenon is configured to distribute pressure longitudinally along the pad body according to a predetermined pressure distribution when the pad body is compressed against the tissue.

Example 2

The ultrasonic surgical instrument of Example 1, wherein the rail and the support base of the tenon are unitarily formed.

Example 3

The ultrasonic surgical instrument of Example 2, wherein the tenon and the pad body are unitarily formed.

Example 4

The ultrasonic surgical instrument of any one or more of Examples 1 through 3, wherein the support base includes a plurality of resilient base members projecting in the transverse direction from the rail.

Example 5

The ultrasonic surgical instrument of Example 4, wherein the plurality of resilient base members have a longitudinal row of resilient base members spaced apart from each other to respectively define the plurality of openings therebetween.

Example 6

The ultrasonic surgical instrument of Example 5, wherein each of the plurality of openings laterally extends through the support base.

Example 7

The ultrasonic surgical instrument of Example 6, wherein each of the plurality of openings laterally extends through an entirety of the second lateral width of the support base.

Example 8

The ultrasonic surgical instrument of Example 4, wherein the support base further includes a buttress extending between the plurality of resilient base members and the rail.

Example 9

The ultrasonic surgical instrument of Example 4, wherein each of the plurality of resilient base members projects in the transverse direction and proximally in the longitudinal direction at a predetermined pitch relative to the pad body, and wherein each of the plurality of resilient base members is configured to resiliently deflect according to the predetermined transverse spring rate in the transverse and longitudinal directions.

Example 10

The ultrasonic surgical instrument of any one or more of Examples 1 through 9, wherein the support base has an elongate support member extending in the longitudinal direction and a plurality of pier members transversely extending between the rail and the elongate support member.

Example 11

The ultrasonic surgical instrument of Example 10, wherein the plurality of openings laterally extend through the support base respectively between the plurality of pier members.

Example 12

The ultrasonic surgical instrument of Example 11, wherein the plurality of openings laterally extend through the support base and the rail.

Example 13

The ultrasonic surgical instrument of any one or more of Examples 1 through 12, wherein the clamp pad further includes an overload surface, wherein the pad body is configured to deflect from a first position toward a second position while supported by the support base with the predetermined transverse spring rate, wherein the overload surface in the first position is disengaged from the clamp arm, and wherein the overload surface in the second position is engaged with the clamp arm for further supporting the pad body.

Example 14

The ultrasonic surgical instrument of Example 13, wherein the pad body has a third lateral width larger than the first lateral width to defines a second shoulder on the pad body, and wherein the second shoulder transversely faces toward the clamp arm and has the overload surface thereon.

Example 15

The ultrasonic surgical instrument of any one or more of Examples 1 through 14, wherein the predetermined pressure distribution is an equalized predetermined pressure distribution such that the predetermined transverse spring rate of the tenon is configured to equalize pressure longitudinally along the pad body when the pad body is compressed against the tissue.

Example 16

A clamp pad for an ultrasonic surgical instrument, comprising: (a) a pad body extending in a longitudinal direction and configured to compress a tissue toward an ultrasonic blade of the ultrasonic surgical instrument; and (b) a tenon secured to the pad body and configured to be received within a mortise of a clamp arm, the tenon including: (i) a rail extending in a transverse direction from the pad body and having a first lateral width in a lateral direction perpendicular to the longitudinal and transverse directions, (ii) a support base extending in the transverse direction from the rail and having a second lateral width in the lateral direction, wherein the second lateral width is larger width is larger than the first lateral width to define a first shoulder configured to engage the clamp arm for securement within the clamp arm, and (iii) a plurality of openings extending through at least one of the support base or the rail such that the tenon has a predetermined transverse spring rate longitudinally along the tenon, wherein the predetermined transverse spring rate of the tenon is configured to equalize pressure longitudinally along the pad body when the pad body is compressed against the tissue.

Example 17

The clamp pad of Example 16, wherein the tenon and the pad body are unitarily formed.

Example 18

The clamp pad of Example 16, wherein each of the plurality of openings laterally extends through the support base.

Example 19

The clamp pad of any one or more of Examples 16 through 18, wherein the predetermined pressure distribution is an equalized predetermined pressure distribution such that the predetermined transverse spring rate of the tenon is configured to equalize pressure longitudinally along the pad body when the pad body is compressed against the tissue.

Example 20

A method of compressing a tissue with an ultrasonic surgical instrument, wherein the ultrasonic surgical instrument includes (a) a shaft assembly; and (b) an end effector extending distally from the shaft assembly and including; (i) an ultrasonic blade, (ii) a clamp arm movably secured relative to the ultrasonic blade and having a mortise longitudinally extending therethrough, and (iii) a clamp pad connected to the clamp arm, including: (A) a pad body extending in a longitudinal direction and configured to compress the tissue toward the ultrasonic blade; and (B) a tenon secured to the pad body and received within the mortise, the tenon including: (I) a rail extending in a transverse direction from the pad body and having a first lateral width in a lateral direction perpendicular to the longitudinal and transverse directions, (II) a support base extending in the transverse direction from the rail and having a second lateral width in the lateral direction, wherein the second lateral width is larger width is larger than the first lateral width to define a first shoulder configured to engage the clamp arm for securement within the clamp arm, and (III) a plurality of openings extending through at least one of the support base or the rail such that the tenon has a predetermined transverse spring rate longitudinally along the tenon, the method comprising: (a) compressing the tissue between the ultrasonic blade and the clamp arm; and (b) resiliently deforming the tenon to according to the predetermined transverse spring rate thereby distributing pressure along the tissue in the longitudinal direction according to a predetermined pressure distribution.

V. Miscellaneous

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 8,623,027; 8,911,460; 9,095,367; 9,393,037; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued by U.S. Pat. No. 8,623,027 on Jan. 7, 2014; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2015/0080924, issued as U.S. Pat. No. 10,172,636 on Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An ultrasonic surgical instrument, comprising:
   (a) a shaft assembly; and
   (b) an end effector extending distally from the shaft assembly and including;
      (i) an ultrasonic blade,
      (ii) a clamp arm movably secured relative to the ultrasonic blade and having a mortise longitudinally extending therethrough, and
      (iii) a clamp pad connected to the clamp arm, including:
         (A) a pad body extending in a longitudinal direction and configured to compress a tissue toward the ultrasonic blade; and
         (B) a tenon secured to the pad body and received within the mortise, the tenon including:
            (I) a rail extending in a transverse direction from the pad body and having a first lateral width in a lateral direction perpendicular to the longitudinal and transverse directions,
            (II) a support base extending in the transverse direction from the rail and having a second lateral width in the lateral direction, wherein the second lateral width is larger than the first lateral width to define a first shoulder configured to engage the clamp arm for securement within the clamp arm, and
            (III) a plurality of openings extending through at least one of the support base or the rail such that the tenon has a predetermined transverse spring rate longitudinally along the tenon,
         wherein the predetermined transverse spring rate of the tenon is configured to distribute pressure longitudinally along the pad body according to a predetermined pressure distribution when the pad body is compressed against the tissue,
         wherein the support base is configured to generate a reactionary force under compression to urge the pad body distally in the longitudinal direction for further securing the clamp pad in the mortise.

2. The ultrasonic surgical instrument of claim 1, wherein the rail and the support base of the tenon are unitarily formed.

3. The ultrasonic surgical instrument of claim 2, wherein the tenon and the pad body are unitarily formed.

4. The ultrasonic surgical instrument of claim 1, wherein the support base includes a plurality of resilient base members projecting in the transverse direction from the rail.

5. The ultrasonic surgical instrument of claim 4, wherein the plurality of resilient base members has a longitudinal row of resilient base members spaced apart from each other to respectively define the plurality of openings therebetween.

6. The ultrasonic surgical instrument of claim 5, wherein each of the plurality of openings laterally extends through the support base.

7. The ultrasonic surgical instrument of claim 6, wherein each of the plurality of openings laterally extends through an entirety of the second lateral width of the support base.

8. The ultrasonic surgical instrument of claim 4, wherein the support base further includes a buttress extending between the plurality of resilient base members and the rail.

9. The ultrasonic surgical instrument of claim 4, wherein each of the plurality of resilient base members projects in the transverse direction and proximally in the longitudinal direction at a predetermined pitch relative to the pad body, and wherein each of the plurality of resilient base members is configured to resiliently deflect according to the predetermined transverse spring rate in the transverse and longitudinal directions.

10. The ultrasonic surgical instrument of claim 1, wherein the support base has an elongate support member extending in the longitudinal direction and a plurality of pier members transversely extending between the rail and the elongate support member.

11. The ultrasonic surgical instrument of claim 10, wherein the plurality of openings laterally extend through the support base respectively between the plurality of pier members.

12. The ultrasonic surgical instrument of claim 11, wherein the plurality of openings laterally extend through the support base and the rail.

13. The ultrasonic surgical instrument of claim 1, wherein the clamp pad further includes an overload surface, wherein the pad body is configured to deflect from a first position toward a second position while supported by the support base with the predetermined transverse spring rate, wherein the overload surface in the first position is disengaged from the clamp arm, and wherein the overload surface in the second position is engaged with the clamp arm for further supporting the pad body.

14. The ultrasonic surgical instrument of claim 13, wherein the pad body has a third lateral width larger than the first lateral width to define a second shoulder on the pad body, and wherein the second shoulder transversely faces toward the clamp arm and has the overload surface thereon.

15. The ultrasonic surgical instrument of claim 1, wherein the predetermined pressure distribution is an equalized predetermined pressure distribution such that the predetermined transverse spring rate of the tenon is configured to equalize pressure longitudinally along the pad body when the pad body is compressed against the tissue.

16. A clamp pad for an ultrasonic surgical instrument, comprising:
  (a) a pad body extending in a longitudinal direction and configured to compress a tissue toward an ultrasonic blade of the ultrasonic surgical instrument; and
  (b) a tenon secured to the pad body and configured to be received within a mortise of a clamp arm, the tenon including:
    (i) a rail extending in a transverse direction from the pad body and having a first lateral width in a lateral direction perpendicular to the longitudinal and transverse directions,
    (ii) a support base extending in the transverse direction and proximally in the longitudinal direction at an oblique angle from the rail and having a second lateral width in the lateral direction, wherein the second lateral width is larger than the first lateral width to define a first shoulder configured to engage the clamp arm for securement within the clamp arm, and
    (iii) a plurality of openings extending through at least one of the support base or the rail such that the tenon has a predetermined transverse spring rate longitudinally along the tenon,
  wherein the predetermined transverse spring rate of the tenon is configured to distribute pressure longitudinally along the pad body according to a predetermined pressure distribution when the pad body is compressed against the tissue.

17. The clamp pad of claim 16, wherein the tenon and the pad body are unitarily formed.

18. The clamp pad of claim 16, wherein each of the plurality of openings laterally extends through the support base.

19. The clamp pad of claim 16, wherein the predetermined pressure distribution is an equalized predetermined pressure distribution such that the predetermined transverse spring rate of the tenon is configured to equalize pressure longitudinally along the pad body when the pad body is compressed against the tissue.

20. A method of compressing a tissue with an ultrasonic surgical instrument, wherein the ultrasonic surgical instrument includes (a) a shaft assembly; and (b) an end effector extending distally from the shaft assembly and including; (i) an ultrasonic blade, (ii) a clamp arm movably secured relative to the ultrasonic blade and having a mortise longitudinally extending therethrough, and (iii) a clamp pad connected to the clamp arm, including: (A) a pad body extending in a longitudinal direction and configured to compress the tissue toward the ultrasonic blade; and (B) a tenon secured to the pad body and received within the mortise, the tenon including: (I) a rail extending in a transverse direction from the pad body and having a first lateral width in a lateral direction perpendicular to the longitudinal and transverse directions, (II) a support base extending in the transverse direction from the rail and having a second lateral width in the lateral direction, wherein the second lateral width is larger than the first lateral width to define a first shoulder configured to engage the clamp arm for securement within the clamp arm, and (III) a plurality of openings extending through at least one of the support base or the rail such that the tenon has a predetermined transverse spring rate longitudinally along the tenon, the method comprising:
  (a) compressing the tissue between the ultrasonic blade and the clamp arm;
  (b) resiliently deforming the tenon to according to the predetermined transverse spring rate thereby distributing pressure along the tissue in the longitudinal direction according to a predetermined pressure distribution; and
  (c) generating a reactionary force under compression that urges the pad body distally in the longitudinal direction further securing the clamp pad in the mortise.

* * * * *